United States Patent [19]

Herlt et al.

[11] Patent Number: 5,342,971
[45] Date of Patent: Aug. 30, 1994

[54] PROCESS FOR THE PREPARATION OF DIBENZO[B,D]PYRANS

[75] Inventors: Tony J. Herlt, Rivett, Australia; Peter L. MacDonald, Gentilino, Switzerland; Rodney W. Rickards, Weetangara, Australia

[73] Assignee: The Australian National University, Canberra, Australia

[21] Appl. No.: 998,046

[22] Filed: Dec. 29, 1992

[51] Int. Cl.$^5$ .......................................... C07D 311/80
[52] U.S. Cl. ................................................. 549/390
[58] Field of Search ........................................ 549/390

[56] References Cited

U.S. PATENT DOCUMENTS

| | | |
|---|---|---|
| 3,919,322 | 11/1975 | Brossi et al. |
| 4,025,516 | 5/1977 | Razdan et al. |
| 4,116,979 | 9/1978 | Razdan et al. |
| 4,381,399 | 4/1983 | Olsen et al. |

FOREIGN PATENT DOCUMENTS

0494665A1  1/1993  European Pat. Off.

OTHER PUBLICATIONS

Chan et al., "A Biomimetic Synthesis of $\Delta^1$-Tetrahydrocannabinol", *Tetrahderon Letters*, vol. 23, No. 29, pp. 2935–2938, Pergamon Press Ltd. (1982).
Crombie et al., "Synthesis of Cannabinoid Methyl Esters and Acids", *J. Chem. Research (M)*, pp. 1301–1345 (1977).
Crombie et al., "Synthesis of Cannabinoid Methyl Esters and Acids", *J. Chem. Research (S)*, pp. 114–115 (1977).
Crombie et al., "Cannabinoid Acids and Esters: Miniatruzied Synthesis and Chromatographic Study", *Phytochemistry*, vol. 16, pp. 1413–1420, Pergamon Press (1977).
Edery et al., "Structure-Activity Relationships in the Tetrahydrocannabinol Series: Modifications on the aromatic ring and in the side-chain", *Arzneim. Forsch.*, pp. 1995–2003 (1972).
Petrzilka et al., "Synthese von Haschisch-Inhaltsstoffen", *Helvetica Chimica Acta*, vol. 52, Fasc. 4, Nr. 123, pp. 1102–1133 (1969).
Razdan et al., "Hashish. A Simple One-Step Synthesis of $(-)$-$\Delta^1$-Tetrahydrocannabinol (THC) from p-Mentha-2,8-dien-1-ol and Olivetol", *Journal of the American Chemical Society*, 96:18, pp. 5860–5865 (Sep. 4, 1974).
Stoss et al., "A Useful Approach Towards $\Delta^9$-Tetrahydrocannabinol", *Synlett*, pp. 553–554 (Aug. 1991).

*Primary Examiner*—Nicky Chan
*Attorney, Agent, or Firm*—Mathews, Woodbridge & Collins

[57] ABSTRACT

Dibenzo[b,d]pyrans are prepared by heating a dihydroxybenzoic acid derivative in the presence of a Lewis acid catalyst and an inert non-polar solvent in which the dihydroxybenzoic acid is soluble but in which the Lewis acid catalyst is insoluble or very slightly soluble. A typical embodiment involves the preparation of intermediates useful in the synthesis of dronabinol and related dibenzo[b,d]pyrans.

8 Claims, No Drawings

PROCESS FOR THE PREPARATION OF DIBENZO[B,D]PYRANS

The present invention pertains to an improved process for the preparation of dibenzo[b,d]pyrans and in particular for the preparation of (6aR, 10aR)-3-alkyl-4-carboalkoxy-6a,7,8,10a-tetrahydro-6,6,9-trimethyl-6H-dibenzo[b,d]pyran-1-ols, valuable intermediates for the production of dronabinol and related compounds.

BACKGROUND OF THE INVENTION

Dronabinol is the United States Adopted name for $\Delta^9$-tetrahydrocannabinol (THC):

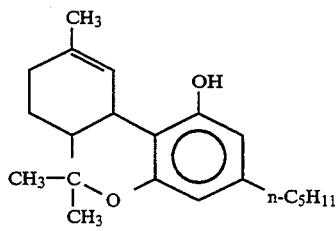

I

Dronabinol recently was included in the United States Pharmacopoeia and currently is in use as an antiemetic for persons undergoing chemotherapy. Other therapeutic applications, including its use as an appetite stimulant in cachectic conditions, also are under investigation.

Previous processes for the preparation of dronabinol and related compounds have employed acid-catalyzed electrophilic condensation of a 5-alkylresorcinol such as 5-n-pentylresorcinol (commonly known as olivetol) and a menthadienol, followed by cyclization; see, e.g., Petrzilka et al., Helv. Chim. Acta, 52, 1102 (1969).

Often the condensation and cyclization are carried out sequentially, without isolation or purification of the intermediate cannabidiols, but this approach suffers from the production of water in the condensation step. This in turn leads to side-reactions during the subsequent cyclization; e.g., isomerization of the double bond from the $\Delta^9$-position to the thermodynamically more stable but unwanted $\Delta^8$-position. Thus the condensation/cyclization conditions employed by Petrzilka et al., supra, cause complete double-bond isomerization, necessitating two additional chemical steps to restore the double bond to the $\Delta^9$-position. The overall yield of dronabinol having a purity greater than 96% thus was reported to be only 17-22% and at least two very tedious and careful chromatographic separations were required. See Razdan et al., JACS, 96, 5860 n.6(b) (1974).

Attempts have been made to absorb the water formed during the condensation step by using various drying agents (anhydrous magnesium sulfate, molecular sieves) Razdan et al., supra, U.S. Pat. No. 4,025,516 and U.S. Pat. No. 4,116,979]. Although on a small scale a 31% yield of reasonably pure dronabinol can be isolated using these techniques, the products are formed as a complex mixture. Moreover when carried out on larger scale, the product mixture still includes significant amounts of $\Delta^8$-tetrahydrocannabinol. See e.g., Olsen et al., U.S. Pat. No. 4,381,399.

Stoss et al., Synlett, 1991, 553, describe a synthesis of dronabinol in which olivetol is condensed with cis-p-menth-2-ene-1,8-diol. See also European Patent Application 494,665. The 6,12-dihydro-6-hydroxycannabidiol intermediate formed, namely 1,3-dihydroxy-2-[6-(2-hydroxyprop-2-yl)-3-methylcyclohex-2-en-1-yl]-5-pentylbenzene, is cyclized with zinc bromide or zinc chloride. An inherent disadvantage of using 6,12-dihydro-6-hydroxycannabidiol involves the water which is formed during the production of $\Delta^9$-tetrahydrocannabinol since, as noted above, water can lead to unwanted side reactions including double-bond isomerization. Although the product after chromatography was stated to contain less than 4% impurities, the level of $\Delta^8$-tetrahydrocannabinol impurity, which is difficult to separate, was not given.

Other processes are generally unsatisfactory for use on an industrial scale because of either or both of the relatively low yields and the formation of large amounts of closely related or isomeric by-products, e.g., abnormal, disubstituted, iso-, cis-, and $\Delta^8$-analogs. Pharmaceutical grade material thus becomes extremely difficult to obtain without resorting to time-consuming, sophisticated, and costly chromatographic purifications; See e.g., Olsen et al, U.S. Pat. No. 4,381,399.

Methyl olivetolate, alternatively named as methyl 2,4-dihydroxy-6-n-pentylbenzoate, has been described as an intermediate in the synthesis of olivetol (see Brossi et al., U.S. Pat. No. 3,919,322) and might be expected, on electronic and statistical grounds, to be less reactive than olivetol towards electrophilic condensation, but to react with greater regiospecificity in producing methyl cannabidiolate:

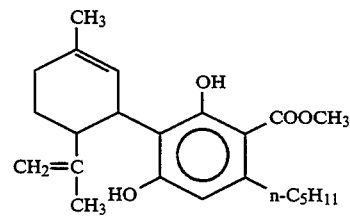

II

This favorable regiospecificity has in fact been observed experimentally by Crombie et al., J. Chem. Res. (S) 114, (M), 1301-1345 (1977) who reported that upon condensation with p-mentha-2,8-dien-1-ol, methyl olivetolate gave methyl cannabidiolate in 89% glc yield (39-56% isolated yield). These yields all are based upon unrecovered starting material, methyl olivetolate. Similar regiospecificity was observed by Crombie et al., Phytochemistry, 16, 1413 (1977) in further studies of this system, although the reaction conditions and product yields varied. Condensation of the corresponding ethyl ester, ethyl 2,4-dihydroxy-6-n-pentylbenzoate, with the same terpene produced up to 63% of the corresponding ethyl cannabidiolate, again based upon unrecovered starting material. In contrast, when olivetol itself was subjected to a similar condensation under a varisty of conditions it consistently yielded less cannabidiol than the corresponding "ortho" isomer. Petrzilka et al., Helv. Chim. Acta, 52, 1102 (1969).

Attempted cyclization of methyl cannabidiolate with p-toluenesulfonic acid, however, was .found by Crombie et al., J. Chem. Res. supra, to produce only about 20% of the desired methyl $\Delta^9$-tetrahydrocannabinolate-B:

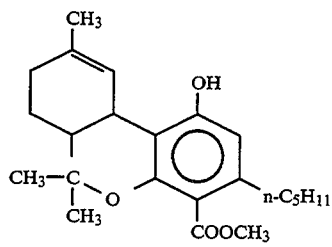
IIIB

The desired product was accompanied by a large quantity and variety of undesired side products including 14% methyl Δ$^9$-tetrahydrocannabinolate-A:

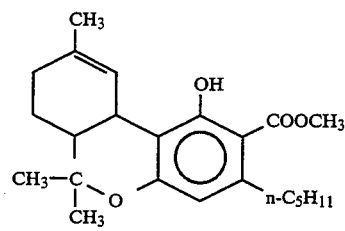
IIIA

In addition, the reaction product included 5% methyl Δ$^8$-tetrahydrocannabinolate-A; 8% methyl Δ$^8$-tetrahydrocannabinolate-B; and 4% of a mixture of methyl isotetrahydrocannabinolate-A and methyl isotetrahydrocannabinolate-B. Moreover, cyclization of methyl cannabidiolate with p-toluenesulfonic acid under somewhat different conditions was found to produce complete double bond isomerization, producing a mixture of methyl Δ$^8$-tetrahydrocannabinolate-A and methyl Δ$^8$-tetrahydrocannabinolate-B with the former predominating {see Edery et al., Arzneim. Forsch. (Drug Res.), 22, 1995 (1972)}. Neither methyl Δ$^9$-tetrahydrocannabinolate-A nor methyl Δ$^9$-tetrahydrocannabinolate-B was found to be produced.

Chan et al., Tetrahedron Letters, 23, 2935 (1982), report to have obtained methyl Δ$^9$-tetrahydrocannabinolate-A directly from methyl olivetolate and p-mentha-2,8-dien-1-ol using boron trifluoride and reaction conditions very similar to those of Crombie et al., Phytochemistry, supra. Numerous attempts to repeat Chan's results have been unsuccessful and rather than producing methyl Δ$^9$-tetrahydrocannabinolate-A, give only methyl cannabidiolate in moderate yield.

Thus previous syntheses of dronabinol utilizing a cannabidiolate intermediate have failed to describe conditions under which the cannabidiolate can be efficiently cyclized to a suitable Δ$^9$-tetrahydrocannabinolate.

DETAILED DESCRIPTION

The present invention pertains to an improved process for the preparation of intermediates useful in the synthesis of dronabinol and derivatives thereof- The cyclization process proceeds with high regioselectivity, yielding no more than about 2% (and generally less) isomeric by-products, and produces the desired product in high yield and purity without any substantial double-bond isomerization.

The process can be diagrammatically represented as follows:

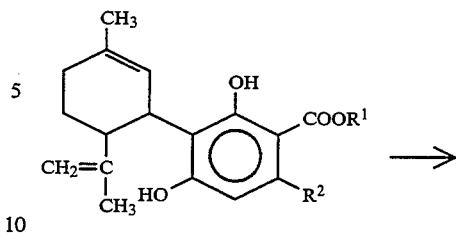
IV

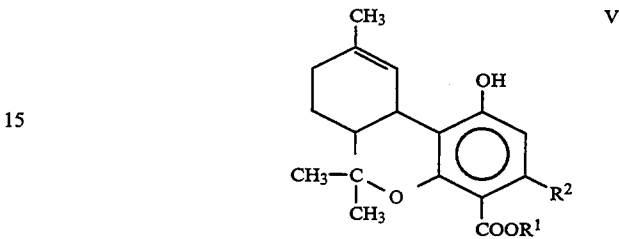
V $R^1$ in the foregoing is a carboxylic acid protecting group, especially lower alkyl of 1 to 12 carbon atoms such as methyl or ethyl and such lower alkyl ester substituted in the 2-position with (i) lower alkoxy, such as for example, methoxymethyl, 1-methoxyethyl, and ethoxymethyl, (ii) lower alkylthio, such as for example methylthiomethyl and 1-ethylthioethyl; (iii) halogen, such as 2,2,2-trichloroethyl, 2-bromoethyl, and 2-iodoethoxycarbonyl; (iv) one or two phenyl groups each of which can be unsubstituted or mono-, di- or tri-substituted with, for example lower alkyl such as tert.-butyl, lower alkoxy such as methoxy, hydroxy, halo such as chloro, and nitro, such as for example, benzyl, 4-nitrobenzyl, diphenylmethyl, di-(4-methoxyphenyl)-methyl; or (v) aroyl, such as phenacyl.

$R^2$ is a straight or branched chain alkyl group having 1 to 10 carbon atoms such as methyl, ethyl, n-propyl, isopropyl, n-butyl, isobutyl, sec-butyl, tert.-butyl, n-pentyl, isopentyl, neopentyl, tert.-pentyl, n-hexyl, isohexyl, heptyl, octyl, nonyl, and decyl.

Preferably $R^1$ is methyl or ethyl and $R^2$ is n-pentyl.

The process is effected through the use of a Lewis acid catalyst which is insoluble or only very slightly soluble in the reaction solvent. Suitable Lewis acids include anhydrous salts of silver, tin, zinc or magnesium, such as for example zinc bromide, zinc iodide, zinc chloride, zinc trifluoromethanesulfonate, magnesium iodide, magnesium bromide, magnesium trifluoromethanesulfonate, stannous chloride, and silver trifluoromethanesulfonate. Particularly preferred are zinc trifluoromethanesulfonate and magnesium trifluoromethanesulfonate.

The process is conducted in the presence of an inert non-polar solvent in which the starting material is soluble but in which the Lewis acid catalyst is insoluble or very slightly soluble such as a aliphatic or aromatic hydrocarbons which is unchlorinated or chlorinated. Suitable solvents include chlorinated hydrocarbons such as dichloromethane, 1,1,1-trichloroethane, and 1,2-dichloroethane, aliphatic hydrocarbons such as heptane, and aromatic hydrocarbons such as benzene, toluene, and xylene. Particularly preferred as solvents are the aromatic hydrocarbons such as toluene.

The process normally is carried out at temperatures operable to effect substantial completion of the reaction within a reasonable time. Such temperatures can range from about 40° to about 200° C., preferably from about 60° to about 120° C.

The cyclization is best carried out under anhydrous conditions. Optionally, a drying agent such as anhydrous magnesium sulphate or molecular sieves is present during the cyclization reaction. An inert atmosphere such as nitrogen can be employed but is not required.

Depending upon the particular Lewis acid used, a small amount, typically less than ten percent, of methyl isotetrahydrocannabinolate-B may be produced during the cyclization. Zinc bromide, for example, is attractive as a catalyst because of its relatively low cost and cyclization with this Lewis acid leads to a reaction product containing no significant impurities other than methyl isotetrahydrocannabinolate-B, typically 6 to 8%. This impurity can be removed without great difficulty prior to the final steps of hydrolysis and decarboxylation using, for example, simple flash chromatography, purification of the intermediate being easier than with the decarboxylated product.

When, on the other hand, zinc or magnesium trifluoromethanesulfonate is used as the Lewis acid catalyst, no significant amount of methyl isotetrahydrocannabinolate-B is formed.

The intermediate obtained according to the present process is of exceptionally high purity and can be converted efficiently into dronabinol or homologs thereof of similar high purity. If desired, the intermediate can be purified further, as for example by flash chromatography, or alternatively, can be used without further purification in this next step.

A further aspect of the invention thus consists of conversion of a compound of Formula IV into dronabinol or a derivative thereof, without any significant degree of double-bond isomerization or other side-reactions, by alkaline hydrolysis and decarboxylation. The present process produces dronabinol or a derivative thereof without any significant amounts of its thermodynamically more stable $\Delta^8$-isomer, which is difficult and expensive to remove. Thus the crude dronabinol produced as the reaction product in the present process typically will contain less than the 2% content of $\Delta^8$-tetrahydrocannabinol permitted by the specifications of the United States Pharmacopoeia.

The examples which follow will serve to further typify the nature of the invention but should not be construed as a limitation on the scope thereof, which scope is defined solely by the appended claims.

EXAMPLE 1

A mixture of methyl cannabidiolate (0.02M) in 1,2-dichloroethane was refluxed with zinc trifluoromethanesulfonate (10 equivalents) and powdered molecular sieves for 48 hours. The reaction mixture was filtered, evaporated, and flash chromatographed on silica gel, eluting with 15% ethyl acetate in hexane to give 71% isolated yield of methyl $\Delta^9$-tetrahydrocannabinolate-B having a purity of 98.8%. The content of methyl isotetrahydrocannabinolate-B was 1.0% and that of $\Delta^8$-tetrahydrocannabinol was less than 1%.

EXAMPLE 2

A mixture of methyl $\Delta^9$-tetrahydrocannabinolate-B (1 part) in methanol (30 parts), water (15 parts), and sodium hydroxide (10 parts) was heated at reflux under a nitrogen atmosphere for 8 hours, cooled, diluted with water, neutralized to pH 7.5 with carbon dioxide, and extracted exhaustively with hexane. The combined extracts were purified by flash chromatography on silica gel using 5% ethyl acetate in hexane to afford dronabinol in 66% yield having a purity of 97.2% (HPLC and GC). The product contained 0.5% $\Delta^8$-tetrahydrocannabinol and 0.5% isotetrahydrocannabinol.

EXAMPLE 3

A mixture of zinc trifluoromethanesulfonate (3.65 g, 10 mmol), powdered 3A molecular sieves (3.64 g), and methyl cannabidiolate (372 mg, 1 mmol) in toluene (50 mL) was stirred at 70° C. for 22.5 hours. The reaction mixture was analyzed by HPLC (column: Merck Lichrosphere DIOL 5 micron, 250×4.0 mm; flow: 1.0 mL/min; solvent: A: hexane, B: 20% tetrahydrofuran in hexane; gradient: 10–40% B, linear, over thirty minutes, then held 10 minutes; detection 228 nm) which was revealed 91.2% methyl $\Delta^9$-tetrahydrocannabinolate-B, 0.2% methyl isotetrahydrocannabinolate-B, 0.3% methyl $\Delta^8$-tetrahydrocannabinolate-B, and 7.2% methyl cannabidiolate. After cooling to room temperature, the reaction mixture was filtered, the residue washed with toluene (5×20 mL), and the combined filtrate and washings evaporated on a rotary evaporator. The crude ester was flushed with nitrogen and dissolved in methanol (10 mL). Aqueous sodium hydroxide (50%, 10 mL) was added and the mixture stirred, refluxed for four hours, and diluted with water (60 mL). The pH was adjusted to 9 with dry ice, the mixture extracted with hexane (3×50 mL), and the hexane extracts dried over sodium sulfate. TLC (dichloromethane-hexane, 1:1, 0.25 mm Merck silica plate) indicated a small amount of cannabidiol present in the crude $\Delta^9$-tetrahydrocannabinol. The amount of cannabidiol can be reduced or eliminated by increasing the reaction time, thereby permitting all the methyl cannabidiolate to react.

The crude product (289 mg) was flashed chromatographed on 230–400 mesh silica On a column of 3 cm i.d. and 20 cm length with 40% dichloromethane in hexane, collecting 20 mL fractions. Fractions 21–30 (153 mg) were free of cannabidiol. Fraction 17–20 (106 mg) still contained traces of cannabidiol by TLC, and were rechromatographed as above to give 97 mg cannabidiol-free material. The yield was 250 mg (79.5%). HPLC analysis (as above but gradient 10–25% B, linear, over twenty minutes, then 25–100% B over one minute and held fifteen minutes) indicated the product was 98.7% pure, containing 0.6% isotetrahydrocannabinol, 0.5% $\Delta^8$-tetrahydrocannabinol, and 0.2% unknown.

The HPLC method described in USP XXII. Sixth Supplement, does not separate isotetrahydrocannabinol from $\Delta^8$-tetrahydrocannabinol. The purity of the product by this method was 98.9% with 1.1% of a mixture of isotetrahydrocannabinol and $\Delta^8$-tetrahydrocannabinol.

EXAMPLE 4

A mixture of magnesium trifluoromethanesulfonate (3.22 g, 10 mmol), powdered 3A molecular sieves (3.64 g), and methyl cannabidiolate (372 mg, 1 mmol) in toluene (50 mL) was stirred at 70° C. for 16 hours, followed by 4 hours at reflux. After cooling to room temperature, the reaction mixture was filtered, the residue washed with toluene (5×20 mL), and the combined filtrate and washings evaporated on a rotary evaporator and flash chromatographed as in Example 1. The product (63% yield) was analyzed by HPLC (column: Merck Lichrosphere DIOL 5 micron, 250×4.0 mm; flow: 1.0 mL/min; solvent: A: hexane, B: 20% tetrahydrofuran in hexane; gradient: 10–40% B, linear, over thirty minutes, then held 10 minutes; detection 228 run) which indicated 99.1% methyl Δ⁹-tetrahydrocannabinolate-B, 0.3% methyl isotetrahydrocannabinolate-B, and 0.6% methyl Δ⁸-tetrahydrocannabinolate-B.

What is claimed is:

1. Process for the preparation of a dibenzo[b,d]pyran of the formula:

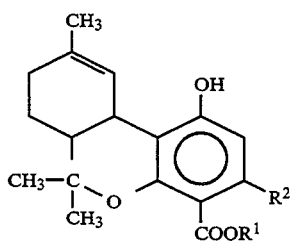

wherein

R¹ is a carboxylic acid protecting group and

R² is a straight or branched chain alkyl group of 1 to 10 carbon atoms, which comprises heating a dihydroxybenzoic acid derivative of the formula:

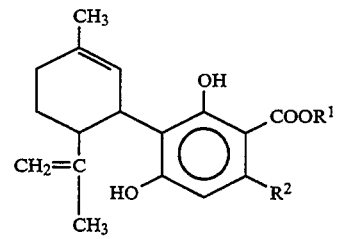

in which R¹ and R² are as herein defined, in the presence of a Lewis acid catalyst and an inert non-polar solvent in which the dihydroxybenzoic acid is soluble but in which the Lewis acid catalyst is insoluble or very slightly soluble.

2. The process according to claim 1 wherein R¹ is lower alkyl of 1 to 12 carbon atoms and R² is n-pentyl.

3. The process according to claim 2 wherein R¹ is methyl or ethyl.

4. The process according to claim 1 wherein the Lewis acid is an anhydrous salt of a metal selected from the group consisting of silver, tin, zinc and magnesium.

5. The process according to claim 4 wherein the Lewis acid is zinc bromide, zinc iodide, zinc chloride, zinc trifluoromethanesulfonate, magnesium iodide, magnesium bromide, magnesium trifluoromethanesulfonate, stannous chloride, or silver trifluoromethanesulfonate.

6. The process according to claim 1 wherein the Lewis acid is a trifluoromethanesulfonate salt of a metal selected from the group consisting of silver, tin, zinc and magnesium.

7. The process according to claim 1 wherein the inert non-polar solvent is an aliphatic or aromatic hydrocarbon which is unchlorinated or chlorinated.

8. The process according to claim 7 wherein the inert non-polar solvent is dichloromethane, 1,1,1-trichloroethane, 1,2-dichloroethane, heptane, benzene, toluene, or xylene.

* * * * *

UNITED STATES PATENT AND TRADEMARK OFFICE
CERTIFICATE OF CORRECTION

PATENT NO. : 5,342,971
DATED : AUGUST 30, 1994
INVENTOR(S) : TONY J. HERLT, PETER L. MACDONALD, RODNEY W. RICKARDS

It is certified that error appears in the above-indentified patent and that said Letters Patent is hereby corrected as shown below:

On the title page item [54],

"DIBENZOIB,DIPYRANS" is changed to -- DIBENZO[b,d]PYRANS --.

On the title page item [56],

<u>Under the heading "Other Publications"</u>:

In the first listed reference, "Tetrahderon" is changed to -- Tetrahedron --. and, Item [57], In the fourth line, the word -- derivative -- is inserted after the word "acid".

Signed and Sealed this

Twenty-first Day of February, 1995

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,342,971
DATED : August 30, 1994
INVENTOR(S) : Tony J. Herlt, et al It is certified that error appears in the above-indentified patent and that said Letters Patent is hereby corrected as shown below:

On the title page, item [73] Assignee, the first-named assignee
--Alco Chemicals, Ltd. Jugano, Switzerland-- is inserted before
(above) "The Australian National University, Canberra, Australia".

Signed and Sealed this

Eighteenth Day of April, 1995

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,342,971

DATED : August 30, 1994

INVENTOR(S) : Tony J. Herlt, et al.

It is certified that error appears in the above-indentified patent and that said Letters Patent is hereby corrected as shown below:

On the title page, item [73]: Assignee, the first-named assignee --Alco Chemicals, Ltd. Lugano, Switzerland-- is inserted before "The Australian National University, Canberra, Australia".

This certificate supersedes Certificate of Correction issued April 18, 1995.

Signed and Sealed this

Twentieth Day of June, 1995

Attest:

BRUCE LEHMAN

Attesting Officer

Commissioner of Patents and Trademarks